US012569232B2

(12) United States Patent
Grüner et al.

(10) Patent No.: US 12,569,232 B2
(45) Date of Patent: Mar. 10, 2026

(54) SURGICAL INSTRUMENT AND STEERING GEAR THEREOF

(71) Applicant: KARL STORZ SE & Co. KG, Tuttlingen (DE)

(72) Inventors: Sven Axel Grüner, Tuttlingen (DE); Dominik Längle, Tuttlingen (DE); Janosz Schneider, Tuttlingen (DE); Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 853 days.

(21) Appl. No.: 17/869,923

(22) Filed: Jul. 21, 2022

(65) Prior Publication Data

US 2023/0030616 A1 Feb. 2, 2023

(30) Foreign Application Priority Data

Jul. 28, 2021 (DE) ..................... 10 2021 119 526.8

(51) Int. Cl.
*A61B 17/00* (2006.01)
*A61B 17/28* (2006.01)

(52) U.S. Cl.
CPC ........ *A61B 17/00234* (2013.01); *A61B 17/28* (2013.01); *A61B 2017/00323* (2013.01); *A61B 2017/00398* (2013.01)

(58) Field of Classification Search
CPC ... A61B 17/28; A61B 17/00234; A61B 34/71; F16H 23/00
See application file for complete search history.

(56) References Cited

U.S. PATENT DOCUMENTS 5,454,827 A 10/1995 Aust et al.
7,699,855 B2 4/2010 Anderson et al.
(Continued)

FOREIGN PATENT DOCUMENTS

DE 102019121092 A1 2/2021
EP 2404713 A1 1/2012
WO WO 2014/004242 A1 1/2014

*Primary Examiner* — Erin McGrath
(74) *Attorney, Agent, or Firm* — Jason H. Vick; Amped IP LLC

(57) ABSTRACT

An exemplary embodiment provides a steering gear (13) for a surgical instrument (1) which has two motorised drives and is designed to spatially align a swash plate (14) via the adjustment angles of the two drives, which is designed to control the distal bending mechanism (9) of the surgical instrument (1). The first drive has a first drive pinion (16) which can be driven by a first motor (17) via a first drive shaft (17*a*) which defines a first drive axis (C) and which is connected to a first drive wheel rim (19) of a first drive wheel (18) in operative connection. The second drive has a second drive pinion (16') which can be driven by a second motor (17') via a second drive shaft (17***a*') which defines a second drive axis (C') and is connected to a second drive wheel rim (19') of a second drive wheel (18') in operative connection. The first and the second drive wheel (18, 18') are designed as double wheels (18, 18'), each of which has the corresponding drive wheel rim (19, 19') and a deviation wheel rim (15, 15'), wherein between the two drive wheels (18, 18') which have a common axis of rotation (A), the swash plate (14) is arranged, and the deviation wheel rims (15, 15') are arranged facing each other on the axis of rotation (A). A surgical instrument (1) with such a steering gear (13**) is also disclosed.

17 Claims, 8 Drawing Sheets

(56)             References Cited

U.S. PATENT DOCUMENTS

| | | | |
|---|---|---|---|
| 7,734,375 | B2 | 6/2010 | Buehler et al. |
| 10,105,128 | B2 | 10/2018 | Cooper et al. |
| 2002/0121152 | A1* | 9/2002 | White .................... F16H 55/18 |
| | | | 74/409 |
| 2005/0275367 | A1* | 12/2005 | Buehler .................. B25J 9/102 |
| | | | 318/568.12 |
| 2017/0281296 | A1* | 10/2017 | Cooper ................. A61B 34/72 |
| 2018/0021960 | A1 | 1/2018 | Grant et al. |
| 2021/0038331 | A1 | 2/2021 | Grüner |

* cited by examiner

SURGICAL INSTRUMENT AND STEERING GEAR THEREOF

CROSS-REFERENCE TO RELATED APPLICATIONS

This application claims the benefit under 35 U.S.C. 119(a) to German Patent Application No. 10 2021 119 526.8, filed 28 Jul. 2021, the disclosure of which is incorporated herein by reference in its entirety.

BACKGROUND

An exemplary embodiment relates to a surgical instrument and a steering gear thereof.

Surgical instruments are known from the prior art which can be guided manually or by a robot and which have tools whose tool tip can be pivoted by means of various pivoting members engaging in one another. These pivot links are connected to a variety of steering wires or cords to provide fine control of the tool tip. A more even force distribution in all bending directions can be achieved with many thin steering wires compared to a few thicker steering wires.

A generic surgical instrument is known, for example, from U.S. Pat. No. 5,454,827, in which the distal pivoting members are coupled via four steering wires to a spatially adjustable swash plate arranged proximally in such a way that a movement of the spatially adjustable swash plate causes a corresponding relative movement of the distal pivoting members and thus a swivelling of the tool tip, wherein the movement of the spatially adjustable swash plate is effected manually via a type of joystick which is coupled directly to the latter.

The design of the drive for the steering wires with the spatially adjustable swash plate, on which all steering wires are mounted, has the advantage that this enables a spatially compact design and only one component has to be moved in order to be able to address all steering wires.

U.S. Pat. No. 7,699,855 discloses a surgical instrument which has an interface in order to be able to connect the instrument to a robotic arm. All drives that control the instrument are arranged in the robotic arm. The angle of rotation of the drives to the instrument is transmitted via coupling disks in a common separating plane.

WO 2014/004242 also describes such an interface, with the drives being installed in the robot arm.

The above design is associated with a complex structure and an indirect backlash control. The drives are not arranged directly in the surgical instrument, which results in a non-linear transmission behaviour when controlling the swash plate, which can only be mapped poorly in software.

U.S. Pat. No. 10,105,128 B2 also discloses a control of such a tool tip; there this is done via a mechanism that includes toothed disk segments and link rods in order to transmit the movement of the drives to the swash plate.

Given this state of the art, the one exemplary aspect is to provide an improved steering gear for a surgical instrument, which has a drive for the spatially adjustable swash plate with linear transmission behaviour and is constructed in a space-saving manner.

This problem is solved by a steering gear with the features of claim 1.

The further object of providing a surgical instrument whose spatially adjustable swash plate is driven by a structurally simple and space-saving steering gear is solved by the surgical instrument having the features of independent claim 10.

Further developments and preferred embodiments of the steering gear and the surgical instrument are set out in the dependent claims.

According to a first embodiment of the steering gear according to an exemplary embodiment for a surgical instrument, this has two motorised drives. It is designed to spatially align a swash plate via the setting angles of the two drives, which is designed to control a distal bending mechanism of the surgical instrument.

According to an exemplary embodiment, the first drive has a first drive pinion which can be driven or driven by a first motor via a first drive shaft and which is operatively connected to a first drive wheel rim of a first drive wheel. The first drive shaft and the first motor define a first drive axis C.

The second drive also has a second drive wheel which can be driven or driven by a second motor via a second drive shaft and which is operatively connected to a second drive wheel rim of a second drive wheel. The second drive shaft and the second motor thereby define a second drive axis C'.

The first and the second drive wheel are designed as double wheels and each have the corresponding drive wheel rim and a deviation wheel rim. The swash plate is arranged between the two drive wheels, which have a common axis of rotation A, wherein the deviation wheel rims is arranged on the axis of rotation A, facing one another.

The steering gear enables a space-saving, in particular axis-parallel arrangement of the drives for controlling the swash plate with economical and backlash-free transmission of the rotary movements of the motors for the spatial alignment of the swash plate.

The drive pinion is preferably designed as a bevel pinion and the drive wheel rim as bevel gear rims, so that the arrangement of the motors, which is offset by 90° in relation to the common axis of the bevel gear rims, with regard to the alignment of the swash plate, saves horizontal installation space in the direction of the common axis A of the bevel gear rims.

Drive wheel rim and deviation wheel rim are preferably arranged on opposite sides of the double wheel, so to speak back to back to one another, with the double wheels being particularly and preferably designed in one piece, which allows a compact and space-saving structure to be achieved.

In a further embodiment of the steering gear according to an exemplary embodiment, the deviation wheel rim and the drive wheel rim of each double wheel have teeth, the number of which is preferably the same. Advantageously, the teeth of the deviation wheel rim and the teeth of the drive rim can then be offset from one another by half a pitch in order to generate a compact double wheel in which the opposing gearings are pushed into one another. "Half pitch" here means an offset of the toothing on a double wheel, which is arranged back to back to each other, as a so-called double-sided bevel gear, wherein a tooth of the inward facing deviation wheel rim towards the swash plate is present in a tooth space of the outward-facing drive gear rim and vice versa. The offset as a circumferential measure corresponds to half a period of the periodic gearing pattern:

$$\text{Offset} = p/2 = \pi \ast d/2z$$

where p is the tooth pitch parameter, which is defined as the arc length on the pitch circle between equal points on two adjacent teeth, d is the corresponding pitch circle diameter and z is the number of teeth. Alternatively, the offset can be defined as an angular offset without reference to the pitch circle diameter, since this can be different for the drive and deviation wheel rims. The angular offset α between the two gearings offset by half a division corresponds to:

$$\alpha=360°/z/2=180°/z.$$

The offset results in a conically converging edge that tapers towards its circumference. This enables a very compact double wheel, which can also do without other components such as spacers. It is also advantageous that the gear flanks can be much thinner than is actually required for power transmission, since the adjacent gear wheels act on one another directly through this thin edge. Since they are only subjected to pressure, comparatively large forces can be transmitted for the small wall thickness. Advantageously, the teeth of the double wheel do not collide with the teeth of other components of the steering gear when these are pushed into one another to reduce the distance. In this way, the axes of both drives can be arranged as close together and compactly as possible around the central axis of the swash plate.

Designing the double wheel with two parallel bevel gear rims on one bearing axis allows the use of standard components and also allows the distance between the drives and the main axis of the instrument to be increased at will, depending on the requirement: For example, if a greater distance of the drive axes from the longitudinal axis of the instrument is necessary or desirable, the gearings, i.e., drive and deviation sprocket, can also be arranged at a greater distance from one another. The bearing can then be located in the area between the teeth. Furthermore, it is possible in an alternative embodiment, if sufficient installation space is available in the direction of the common axis A, for the double wheel to have a waist in the axial direction, with the deviation wheel rim being spaced from the drive wheel rim, which then points in the opposite direction towards the deviation wheel rim or, like the deviation wheel rim, inwards the swash plate. By dimensioning the distance provided by the waist between the deviation wheel rim and the drive wheel rim accordingly, the drive pinion that is operatively connected to the drive wheel rim is arranged in the area of the waist between the deviation wheel rim and the drive wheel rim.

In yet another embodiment of the steering gear according to an exemplary embodiment, each double wheel is arranged on a bearing axis which defines the common axis A and which is designed as an axis stub at its free end pointing away from the double wheel. In other words, in this embodiment, the bearing axis is connected to the double wheel in a torque-proof manner and can preferably be manufactured in one piece with it. The axis stub formed on the free end of the bearing axis pointing away from the double wheel carries a bearing ring, which preferably provides a ball bearing or a roller bearing. The bearing ring is part of a fastening device and is fixed to it. The fastening device is also firmly connected to a housing component of the steering gear. The double wheels can be mounted firmly in the housing of the steering gear via the bearing, so that the axis position and axial position of the double wheels are defined.

Alternatively, a further embodiment of the steering gear according to an exemplary embodiment provides that the or each double wheel is arranged on a bearing axis on the housing side, wherein a bearing ring is arranged coaxially on the bearing axis at an end pointing towards the double wheel, which can be designed accordingly as an axis stub with a bearing seat, in a concentric bearing recess of the double wheel. Here, too, the bearing ring preferably provides a ball bearing or a roller bearing. In this embodiment, the bearing axis with the axis stub on which the double wheel is rotatably mounted can, for example, be designed in one piece with a housing component and thus be part of the housing. This embodiment prevents the double wheel from tilting about the bearing seat. Furthermore, in a modification of this embodiment, the bearing axis can have a thread at its free end (i.e., the end of the axis that does not carry the double wheel), which engages with a counter-thread of a fastening device, wherein the fastening device is part of the housing or fixed connection to a housing of the steering gear. This two-part design of the bearing axis and housing component, so that the bearing axis can be adjusted against the housing via the thread, enables an optimal adjustment of the bearing axis and thus the arrangement of the double wheels in the steering gear.

If necessary, the aforementioned alternative storage variants can also be combined in a steering gear, so that one of the double wheels is designed with an axis stub that is rotatably mounted in a bearing device of the housing, and the other double wheel is designed with a bearing recess in which a bearing for the rotatable receiving of a stub axis is arranged, which is part of a housing component or, for example, is connected via thread.

In a further embodiment of the steering gear according to an exemplary embodiment, the swash plate can be coupled to a third gear wheel. The third gear wheel as part of the swash plate mechanism meshes with the two deviation wheel rims of the two double wheels. The axis of rotation D of the third gear wheel is at right angles to the common axis A of the driven double wheels. Each movement of the two driven gear wheels is advantageously transmitted directly to the third gear wheel, which is coupled to the three-dimensionally adjustable swash plate, by the three meshing gear wheels. Although the double wheels can be designed with a thin wall thickness in the toothing area, comparatively large forces can be transmitted between the gear wheels, since the gearing is only subjected to pressure.

Furthermore, in a further embodiment of the steering gear according to an exemplary embodiment, the swash plate can be coupled to a fourth gear wheel, which is coupled to the two bevel gear rims of the two double wheels and is arranged on the opposite side of the third gear wheel. This closes the circulating gearing chain and ensures an even, circulating and backlash-free distribution of force.

In the case of the particularly compact design of the double wheel with the teeth of the drive and deviation sprocket rim offset by half a pitch width, so that the sprockets are pushed into one another, a straight toothing may be preferred, so that the drive pinion and the third and optionally fourth sprocket are also straight-toothed. In yet another embodiment of the steering gear according to an exemplary embodiment, which can also include double wheels that deviate from the particularly compact design, the bevel gears installed in the steering gear, be it the drive pinion, drive and deviation wheel rim of the two double wheels or also the third or fourth gear wheel, are provided with bevel gear rims, which can be straight-toothed, helical-toothed, spiral-toothed or eccentrically hypoid-toothed in variants that are coordinated with one another. The advantage of this is that, depending on the design, smooth running can be achieved. In the case of eccentric hypoid gearing, in which the drive pinion and the drive wheel rim form a bevel helical gear or hypoid gear, which has an axis offset, i.e., in which the drive axis C and the common axis A of the double wheels do not intersect, the axes of rotation of the drives can also be used before or behind the plane of the steering gear, which is spanned by the axis of rotation of the instrument or the central axis of the swash plate and the axis of rotation of the third and fourth gear wheel, which enables specific designs of the steering gear.

A further embodiment of the steering gear according to an exemplary embodiment provides that each of the motors can be arranged radially pointing away from the respective drive wheel rim via its respective drive pinion in any position along the circumference of the double wheel. Any arrangement of the drives around the common axis of rotation of the double wheels in combination with a suitable gearing of the bevel gear rims allows a large number of different arrangements.

In a preferred embodiment of the steering gear according to an exemplary embodiment, the two drive axes C, C' can run parallel to one another, wherein the drive axes running perpendicular, i.e., at right angles, to the common axis A; the motors can be arranged next to one another in a particularly space-saving manner. A so-called axis-parallel arrangement of the motors enables a compact and thus space-saving arrangement of the components of the steering gear. Furthermore, due to the parallel arrangement of the motors, an arrangement close to the main axis of the surgical instrument is achieved and the power transmission is thus improved.

One exemplary embodiment also relates to a surgical instrument which has a shaft, an actuation unit arranged at the proximal end of the shaft and a tool arranged at the distal end of the shaft. The tool has a tool tip that can be angled using a distal bending mechanism. The bending mechanism can be controlled or aligned by a swash plate that can be spatially aligned by means of two drives, for which purpose the surgical instrument has a steering gear according to an exemplary embodiment, the two drives being part of the steering gear according to an exemplary embodiment, which is designed to adjust the adjustment angles of the two drives to the spatial alignment to the swash plate so as to control the bending mechanism.

Due to the steering gear according to an exemplary embodiment, the surgical instrument can be constructed in a structurally simple and space-saving manner, so that a simple connection to a robot arm can be made possible, in which the movement of the drives can be transmitted linearly to the tool tip. The result is an exactly controllable use of the surgical instrument.

In order to be able to three-dimensionally adjust the spatially adjustable swash plate despite the non-rotatable coupling with the third gear wheel, which meshes with the two bevel gear rims of the two double wheels, i.e., to be able to superimpose the tilting or pivoting movements with a rotation of the swash plate around the longitudinal axis, a preferred embodiment of the surgical instrument can provide that the swash plate is rotatably mounted about the longitudinal axis B of the shaft via a bearing ring in a steering ring, which is non-rotatably coupled to the third gear wheel. For the rotational coupling of the swash plate to a main shaft running coaxially to a longitudinal axis B of the shaft, the swash plate can be cardanically coupled to the main shaft.

To form the cardan mounting of the spatially adjustable swash plate, an embodiment of the surgical instrument according to an exemplary embodiment can provide that the swash plate is pivotably mounted on a universal joint disk via two bearing pins arranged offset by 180° to one another; the universal joint disk being pivotable via two bearing pins arranged offset by 180° to one another is mounted on the main shaft and wherein the bearing pins of the swash plate and the universal joint disk are offset by 90° to each other. The cardan suspension enables movement in all three spatial axles, which means that the tool tip can be controlled in a targeted manner. As an alternative to a universal joint disk with two pairs of pins crossed at right angles for the cardan mounting of the swash plate on the main shaft, an advantageous embodiment can provide that the main shaft has two guide grooves in its outer surface for the cardan mounting, which extend diametrically and longitudinally of the main shaft; the swash plate, which is annular with an outer side and an inner side, has two diametrically and radially inwardly arranged pins on the swash plate. Each of the two pins permanently mounted on or in the swash plate engages in one of the guide grooves on both sides of the main shaft, so that a rotation angle of the shaft can be transferred to the swash plate. This advantageously results in a torsionally stiff connection between the main shaft and the swash plate, which allows a transmission of the angle of rotation even with a large angular misalignment (±40° and more) and axial misalignment, while being very compact and easy to manufacture and assemble. In principle, however, a curved tooth coupling can also be used for the cardan mounting of a swash plate on a main shaft despite a relatively small angular misalignment, a constant velocity joint despite the complex manufacturing process and complex assembly, or a material-to-material coupling, which is often associated with a backlash rotational angle transmission.

In a further embodiment of the surgical instrument according to an exemplary embodiment, steering wires which are connected to the swash plate of the steering gear run in the longitudinal direction of the shaft. The fact that the steering ring is mounted in a bearing ring which is non-rotatably coupled to the third gear wheel has the effect that the twisting of the steering wires is prevented, more advantageously for pivoting the tool tip relative to the longitudinal axis and rotating about the longitudinal axis of the shaft.

The advantage of this construction compared to known constructions is that not only the use of a small number of steering wires, namely only four steering wires, and an exclusively manual actuation of the spatially adjustable disk serving as a drive for the steering wires is possible, but that a large number of steering wires can be chosen freely and thus a sensitive and reproducible adjustment of the distal-side pivoting members is possible.

Moreover, a further embodiment of the surgical instrument according to an exemplary embodiment provides that the fourth gear wheel with the swash plate is coupled to the steering ring via a bearing ring, with the fourth gear wheel being freely rotatable relative to the third gear wheel. This fourth gear wheel closes the revolving gearing chain and thus ensures an even revolving and backlash-free power distribution.

In a further embodiment of the surgical instrument according to an exemplary embodiment, an actuation element is mounted in the shaft in an axially displaceable manner and is operatively connected to the actuation unit on the proximal side. The distal bending mechanism of the deflectable tool tip consists of pivoting members arranged at the distal end of the shaft, which are connected to the steering gear via the steering wires running in the longitudinal direction of the shaft. In one embodiment, the steering wires can be releasably fixed to the swash plate, for example by means of a clamp connection, so that the steering wires can be easily replaced in the event of damage.

In a further embodiment of the surgical instrument according to an exemplary embodiment a radial distance between the steering wires and the longitudinal axis of the shaft on the swash plate is greater than at the proximal end of the shaft from which the steering wires emerge. The steering wires may extend from the proximal end of the shaft directly to the swash plate, with the steering wires meeting the swash plate at an angle other than 90°. Alternatively, a wire spreader can be arranged on the main shaft on the distal side in front of the swash plate, which increases the radial distance of the steering wires emerging from the proximal shaft end from the longitudinal axis of the shaft, so that the steering wires between the wire spreader and the swash plate run approximately parallel to one another and in relation to one another form an angle of approx. 90°. Due to the lower installation space requirement, the variant without a wire spreader may be preferred. Increasing the radial distance of the steering wires from the longitudinal axis of the shaft, from a diameter of 4 mm to a diameter of 18 mm, for example, not only simplifies the assembly and manufacture of the steering wire drive, which is equipped with the spatially adjustable disk, but also the adjustment angle of the spatially adjustable disk or, as a result of the enlarged lever, it reduces the forces required for bending in order to achieve a pivoting angle of the tool tip that corresponds to the extent of the increase in diameter.

In order to avoid a collision of the gears with the steering wires and possibly the actuation element when pivoting the third and fourth gear wheel relative to the longitudinal axis of the shaft, recesses for the steering wires and the actuation element can be formed in the sprockets of the third gear wheel and the fourth gear wheel.

The surgical instrument according to an exemplary embodiment has the advantage that many thin steering wires can be used to control the pivotable tool tip and this control is sensitive, exact and reproducible due to the motorised drive for the spatially adjustable disk on which the steering wires are mounted on the proximal side.

BRIEF DESCRIPTION OF THE DRAWINGS

Other embodiments of the steering gear and the surgical instrument, as well as some of the advantages associated with these and other embodiments, will become apparent and better understood from the following detailed description with reference to the accompanying figures. Items or parts thereof that are substantially the same or similar may be given the same reference numbers. The figures are only a schematic representation of an exemplary embodiment. Showing.

DETAILED DESCRIPTION

Figure 1:
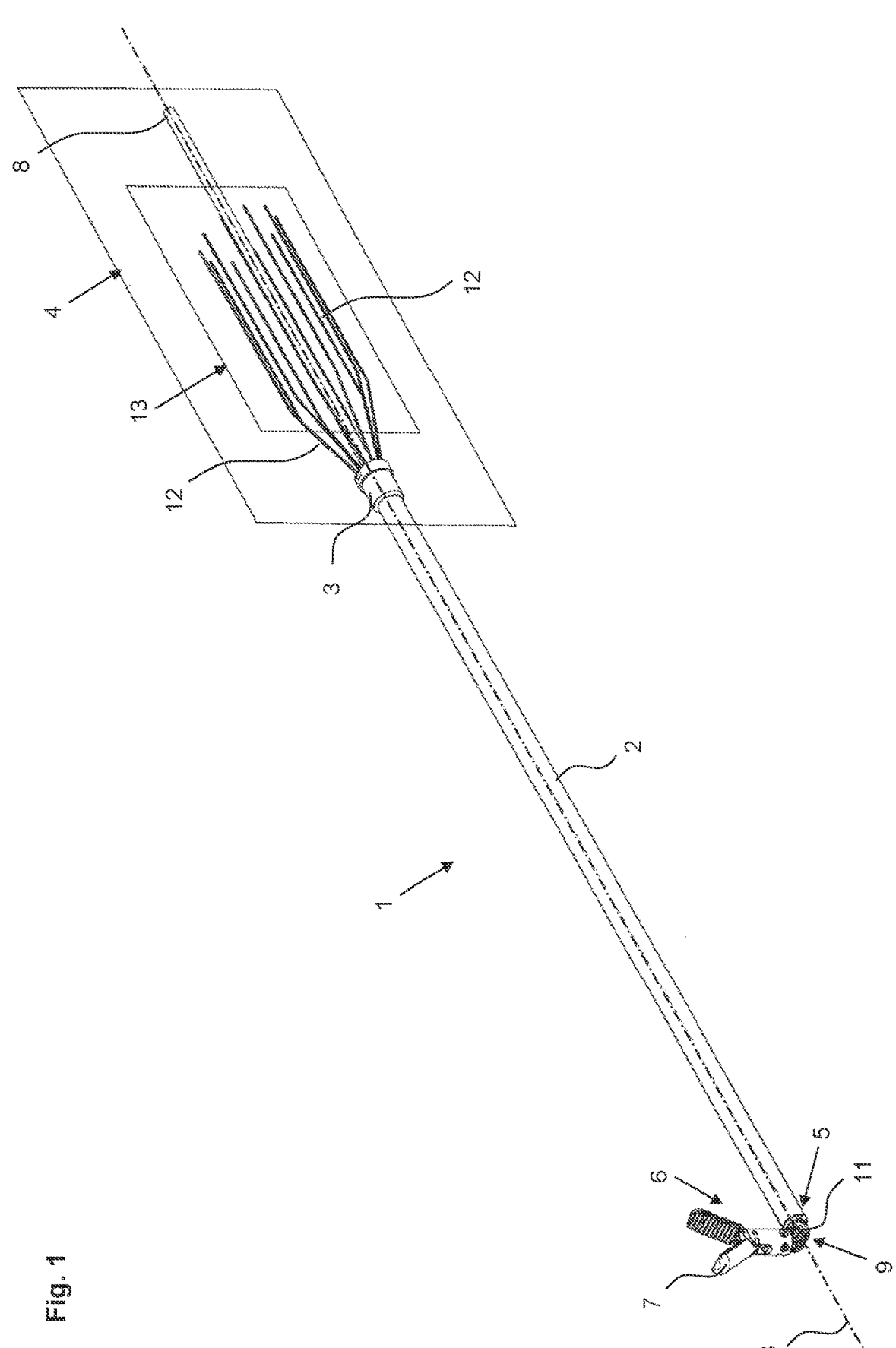
FIG. 1 a perspective view of the surgical instrument with the actuation unit shown schematically, FIG. 2 a perspective view of a first embodiment of the steering gear according to an exemplary embodiment with motors arranged perpendicularly to the instrument axis B, FIG. 3 a top view of yet another embodiment of the steering gear according to an exemplary embodiment with motors arranged parallel to the instrument axis B, FIG. 4 a perspective, partially cut-out view of a further embodiment of the steering gear according to an exemplary embodiment without showing the motors and drive pinions with an enlarged detailed view of the swash plate bearing, FIG. 5 a perspective detailed view of one of the two double wheels, FIG. 6 a further embodiment of the double wheel with a correspondingly engaging drive pinion in eccentric hypoid gearing, FIG. 7 a detailed bottom view of the engagement of the drive pinion with the deviation wheel rim and the drive wheel rim with the third gear wheel of the steering gear from FIG. 2, FIG. 8 a perspective, partially cut-out detailed view of the swash plate mechanism in an alternative embodiment, FIG. 9 a detailed plan view of a double wheel in engagement with the drive pinion and the fourth gear wheel according to a further embodiment, FIG. 10 a detailed plan view of a double wheel in engagement with the drive pinion and the fourth gear wheel according to a further embodiment.

FIG. 1 shows a surgical instrument 1 with a hollow shaft 2, which has a schematically illustrated actuation unit 4 arranged at the proximal end 3 of the shaft 2 and a tool tip 6 arranged at the distal end 5 of the shaft 2. The tool tip 6 is connected to a tool 7 which can be actuated via an actuation element 8 which is mounted in the shaft 2 in an axially displaceable manner and which is in operative connection with the actuation unit 4 on the proximal side. The actuation unit 4 can be a manually actuable handling or a unit designed for robotic use, that is, one that can also be actuated without manual intervention.

The tool 7 of the tool tip 6 can, for example, be a tool provided with jaw parts, as shown in FIG. 1, or act as an endoscope, an applicator or the like.

The instrument tip 6 can be pivoted relative to the longitudinal axis B of the shaft 2 via a joint mechanism 9, wherein the joint mechanism 9 consists of pivoting members 11 arranged at the distal end of the shaft 5, which are connected via guide wires 12 or guide ropes running in the longitudinal direction of the shaft 2 with a drive 13 arranged at the proximal end 3 of the shaft 2, which causes a movement of the drive 13 on the proximal side and corresponding relative movements of the pivoting members 11 on the distal side and thus a pivoting of the instrument tip 6.

Even if only the term steering wires is used above and below, steering cables can also be used functionally, which is why the term steering wires is also to be understood herein synonymously as steering cables.

The actuation element 8, which is mounted so that it can be axially displaceable in the shaft 2 for actuating the tool 7, which consists of two jaw parts for example, is designed as a push/pull rod in the illustrated embodiment.

The drive for the steering wires 12 is designed as a motorised drive in the surgical instrument 1 shown in the figures and described below.

The core of the drive is a spatially adjustable swash plate 14 (FIGS. 2 to 4 and 8) to which the steering wires 12 are attached in such a way that a displacement of the swash plate 14 causes the tool tip 6 to pivot via the steering wires 12 attached to it. With the motorised drive, the swash plate 14 can be displaced; with it, it is possible to control the steering wires 12 for pivoting the distal-side pivoting members 11 or the tool tip 6 precisely, sensitively in the smallest of steps and also reproducibly. In addition, the number of steering wires 12 to be used for a motorised steering gear 13 can be chosen quite freely.

Figure 2:
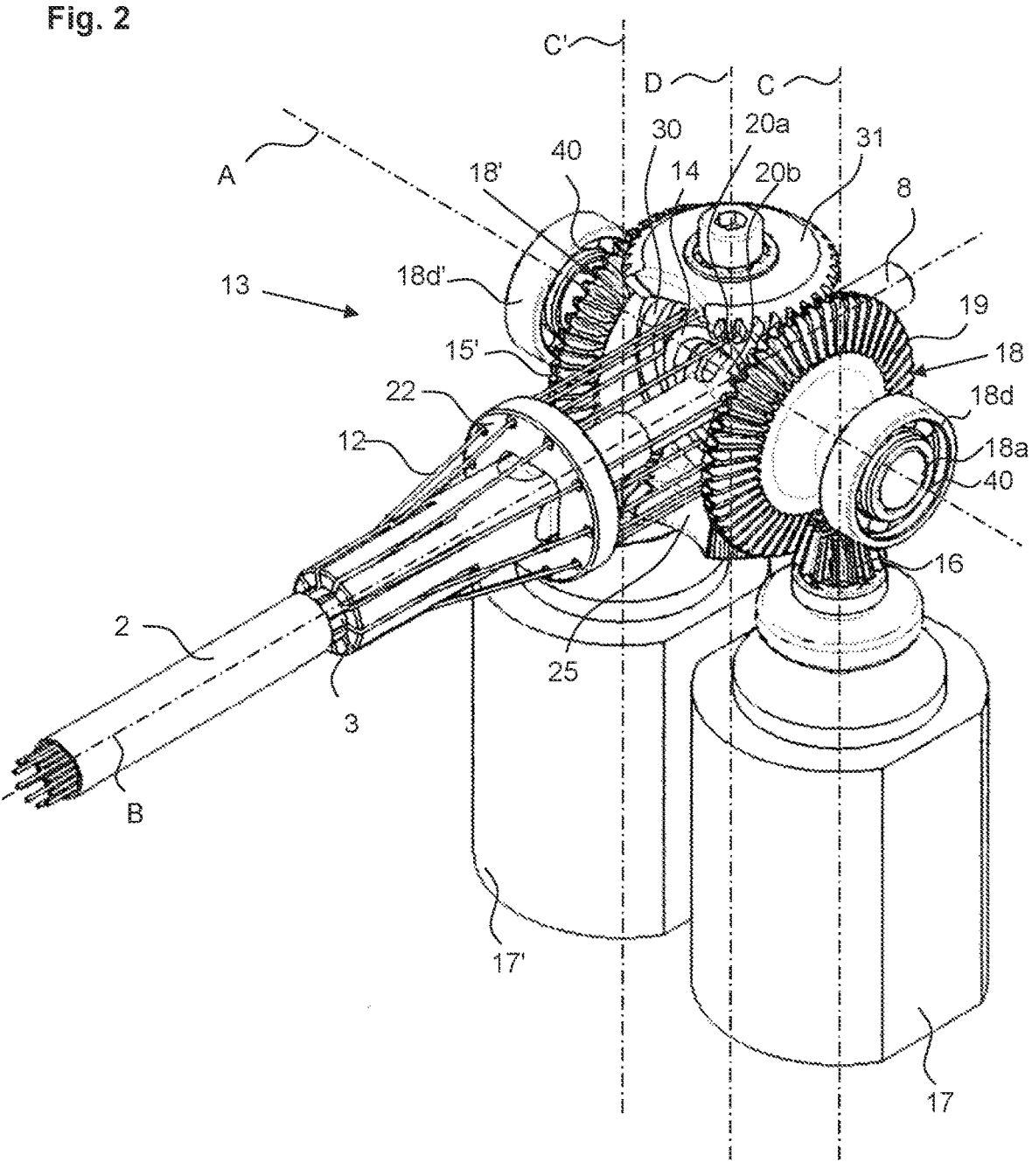
Figure 3:
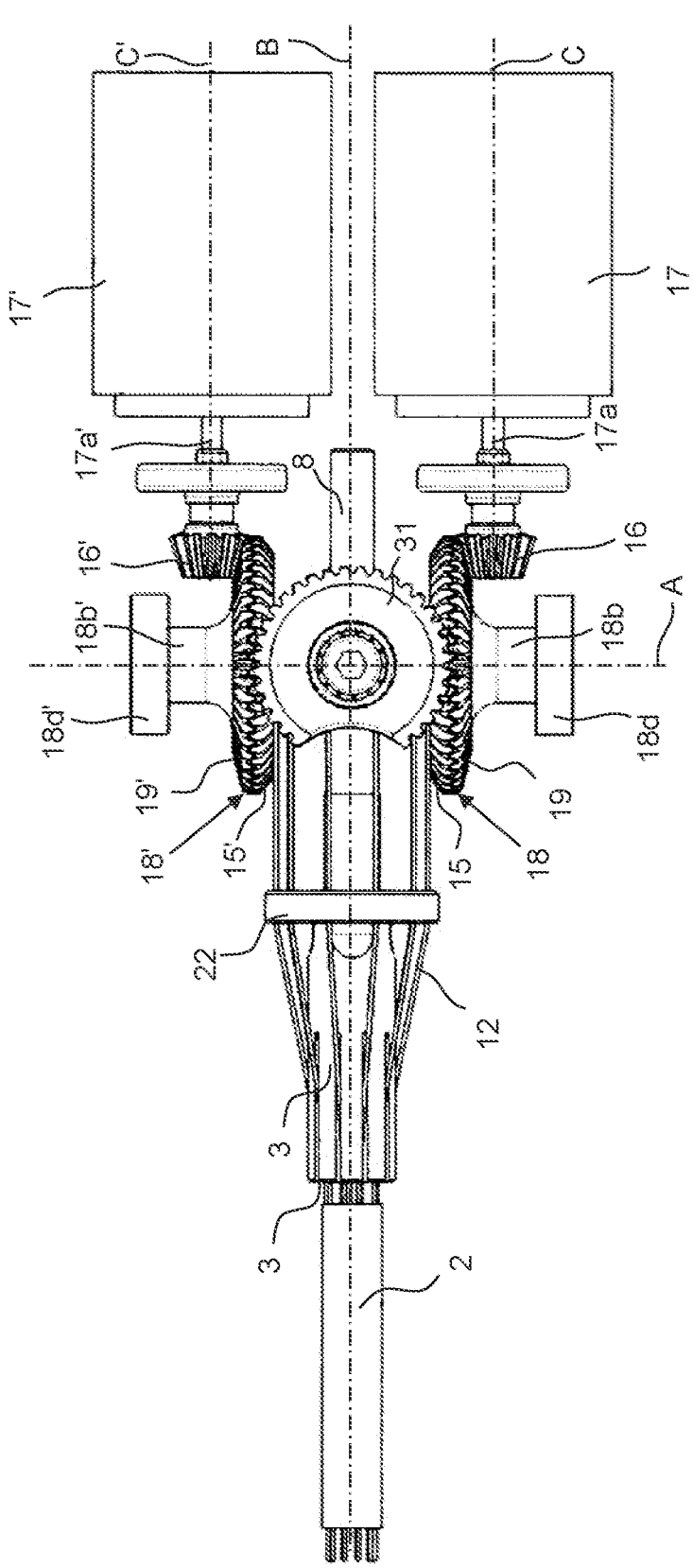

In FIGS. 2 to 4 and 8 the steering gear 13 is shown in simplified form, the steering gear 13 having the swash plate 14 in the middle. With the swash plate 14 four gear wheels are connected in the example shown. A third gear wheel 25 and a fourth gear wheel 31 are disposed below and above the swash plate 14 and operatively coupled to the swash plate 14. That is, a movement of one of these gear wheels 25, 31 has a direct movement of the swash plate 14 as result. Double wheels 18, 18' arranged on the left and right side engage in the gear wheels 25, 31. For this purpose, the double wheels 18, 18' have deviation sprockets 15, 15' designed as bevel gear rims, which engage directly in the sprockets of the gear wheels 25, 31, which are executed as partial bevel gear rims, i.e., the bevel toothing are not circumferential, but are only present in the engagement with the double wheels 18, 18' for the intended range of movement in required peripheral sections. The double wheels 18, 18' have drive wheel rims 19, 19', which are also bevel gear rims, on sides pointing away from each other along their centre axis A, which also forms the common axis of rotation A of both double wheels 18, 18'. A drive pinion 16, 16', which is correspondingly designed as a bevel pinion, meshes with each of these drive wheel rims 19, 19'. This drive pinion 16, 16' is arranged with its axis of rotation or drive C, C' at a 90° angle to the axis of rotation A of the double wheels 18, 18' and can be orientated in a plane parallel to the longitudinal axis B along the circumference of the double wheels 18, 18'. For example, each drive axis C, C' can also lie at a 90° angle to the longitudinal axis B of the instrument 1 (e.g., FIGS. 2 and 7) or parallel to it. The latter is shown in FIG. 3, wherein a drive axis of the drive pinions 16, 16' (axis of rotation C and C') runs parallel to the longitudinal axis B of the instrument. The drive pinions 16, 16' are driven by motors 17, 17', the drive pinions 16, 16' sitting on drive shafts 17a, 17a' which are directly connected to the motors 17, 17'. The axis of rotation C, C' of the drive pinions 16, 16' is the same as the axis of rotation of the motors 17, 17'.

Of course, arrangements of the motors 17, 17' and the drive bevel gears 16, 16' that deviate from the examples shown are also conceivable. The arrangement of the drive units consisting of the motor and the drive pinion can be freely selected along the circumference of the respective double wheel, so that an existing installation space can be optimally used, or the dimensions of the actuation unit can be reduced. That is, the axes of rotation C, C' do not have to be parallel to the longitudinal axis B of the instrument, but can theoretically be arranged in any orientation and also independently of one another on the double wheels 18, 18'. However, the illustrated arrangement examples from FIGS. 2 and 3 may be preferred for design reasons: Both by the perpendicular arrangement of the motors 17, 17' to the longitudinal axis B, shown side by side in FIG. 2, and also by the arrangement of the motors 17, 17' parallel to the longitudinal axis B in FIG. 3, the construction height is reduced. However, it is also conceivable that one of the motor and drive pinion drive units is offset by 180° with respect to the double wheels 18, 18', so that the motor-bevel pinion arrangements are diametrically offset and point in opposite directions, in particular in relation to the longitudinal axis B with the parallel arrangement of the motors 17, 17', since this does not increase the overall height.

The double wheels 18, 18' are driven by motors 17, 17' via the drive pinions 16, 16' attached to the drive shafts 17a, 17a' of the motors 17, 17', the axis of rotation of which corresponds to an axis of rotation C, C' that the motors 17, 17' are equivalent to. By turning the drive pinion 16, 16', which engages in the drive wheel rim 19, 19' of the respective double wheels 18, 18', the double wheel 18, 18' is moved in correspondence in a gear ratio between the drive pinion 16, 16' and the drive wheel rim 19, 19'. Due to the design as a bevel gear, the rotation of the motors 17, 17' and thus the drive pinions 16, 16' about the drive axis C, C' is transferred to a rotation of the double wheels 18, 18' about their axis of rotation A. The rotary movement of the double wheels 18, 18' then causes a rotary movement of the third gear wheel 25 or the fourth gear wheel 31 about their axis of rotation D, which is at right angles to the common axis A of the double wheels 18, 18', and thus a movement of the swash plate 14.

Figure 4:
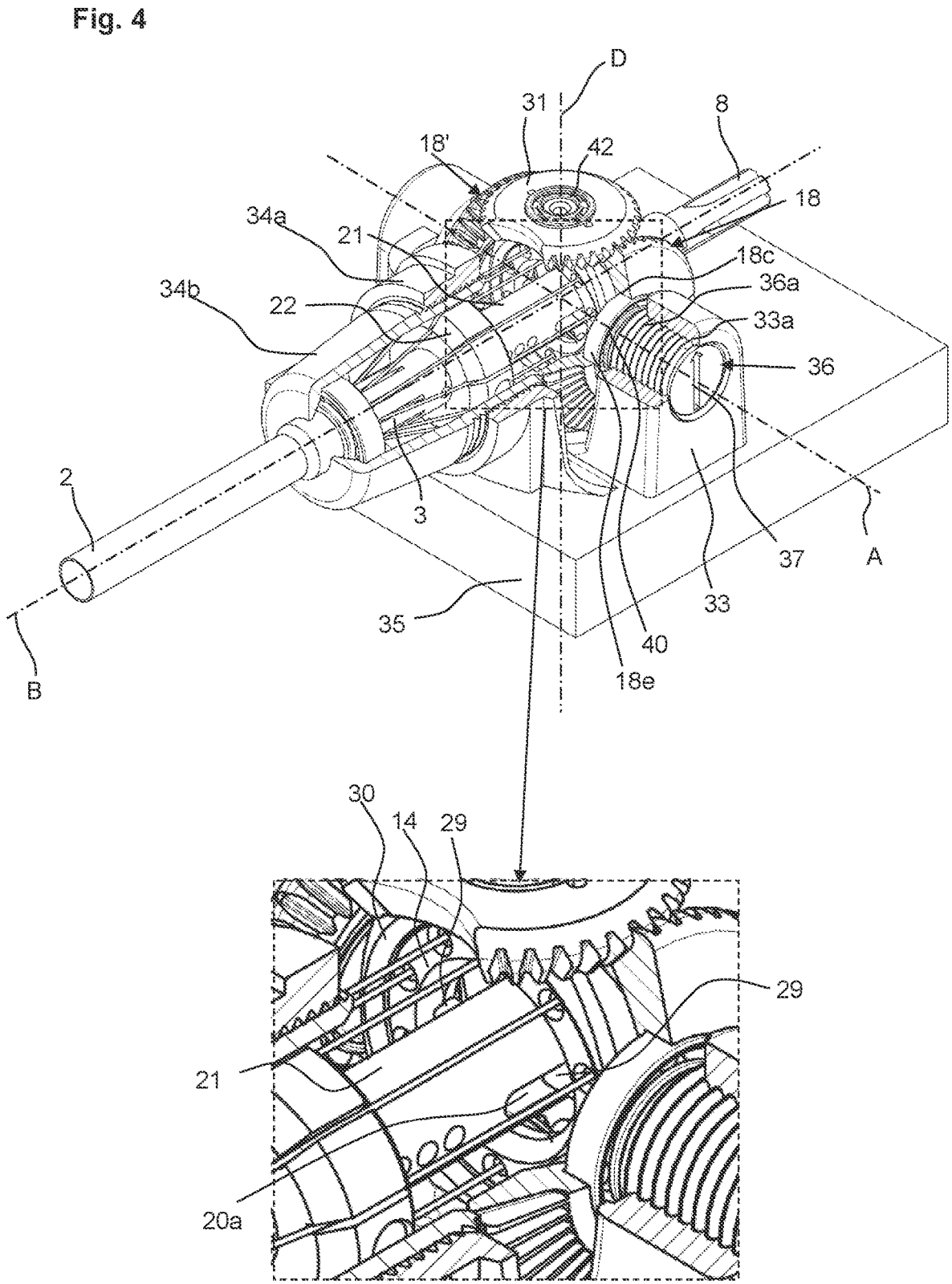
Figure 5:
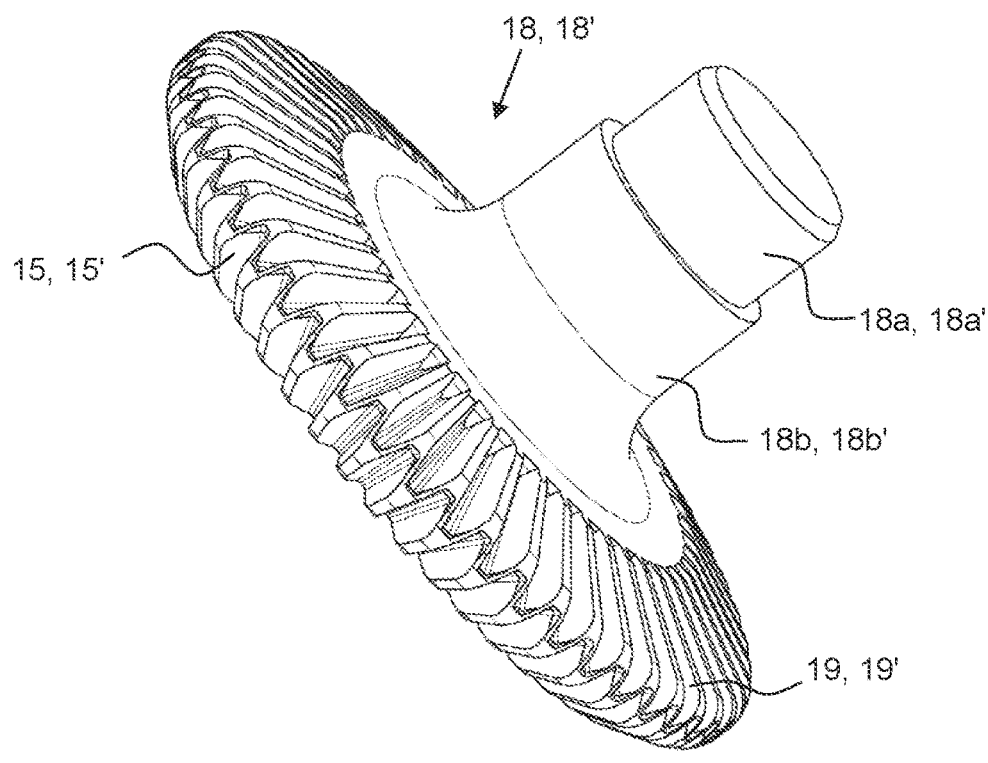
Figure 6:
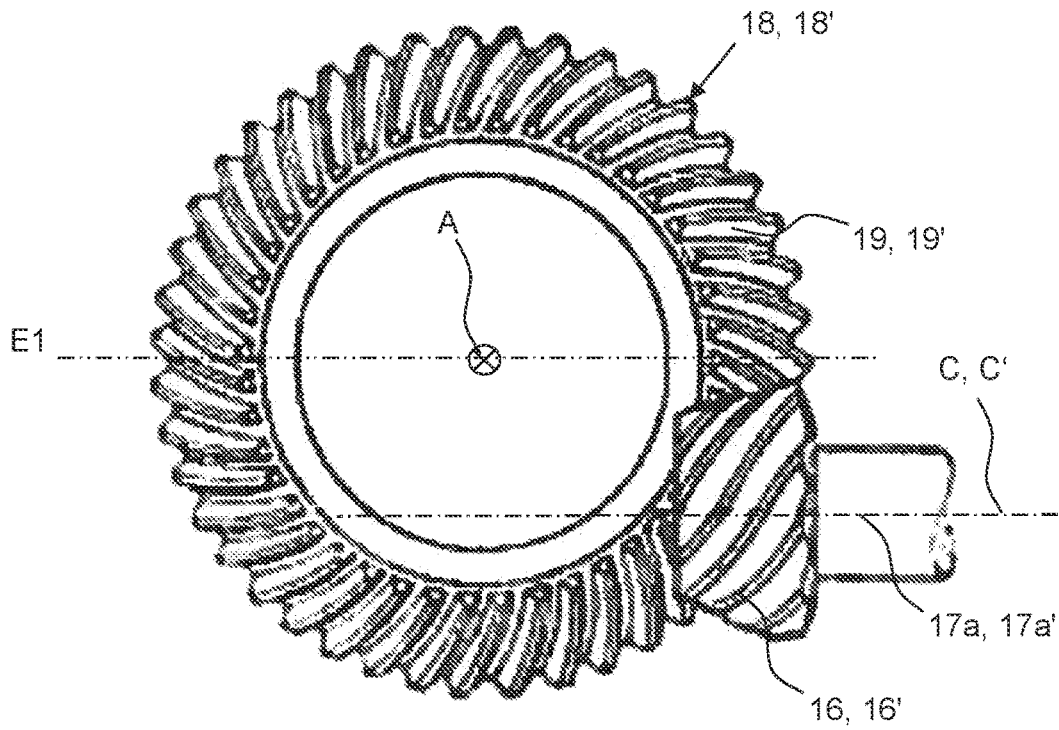

In FIGS. 5 and 6 two types of double wheels 18, 18' are shown. FIG. 5 illustrates a preferred double wheel 18, 18', which is also set in the examples of FIGS. 2-4 and 7 and has a drive wheel rim 19, 19', and the deviation rim 15, 15' is present on its rear side, so that both wheel rims 15, 15', 19, 19' come to rest back to back. Both the drive and deviation wheel rims 15, 15', 19, 19' have straight bevel toothing, in which the teeth run straight radially outwards.

In FIG. 6 an alternative gearing of drive wheel rim 19, 19' of a double wheel 18, 18' with a drive pinion 16, 16' is shown, which is designed as helical bevel gearing or hypoid gearing. Due to the eccentric arrangement of the drive axes C, C', which does not intersect the common axis A running perpendicular to the plane of the drawing plane, the drive shaft 17a, 17a' of the drive pinion 16, 16' is arranged parallel to an imaginary plane E1 of the steering gear 13, which is defined through the common axis A and the longitudinal axis B or through the common axis A and an axis perpendicular to the common axis A and the longitudinal axis B (the axis of rotation D in FIGS. 2 and 4 corresponds to the swash plate 14 in the neutral position).

Figure 7:
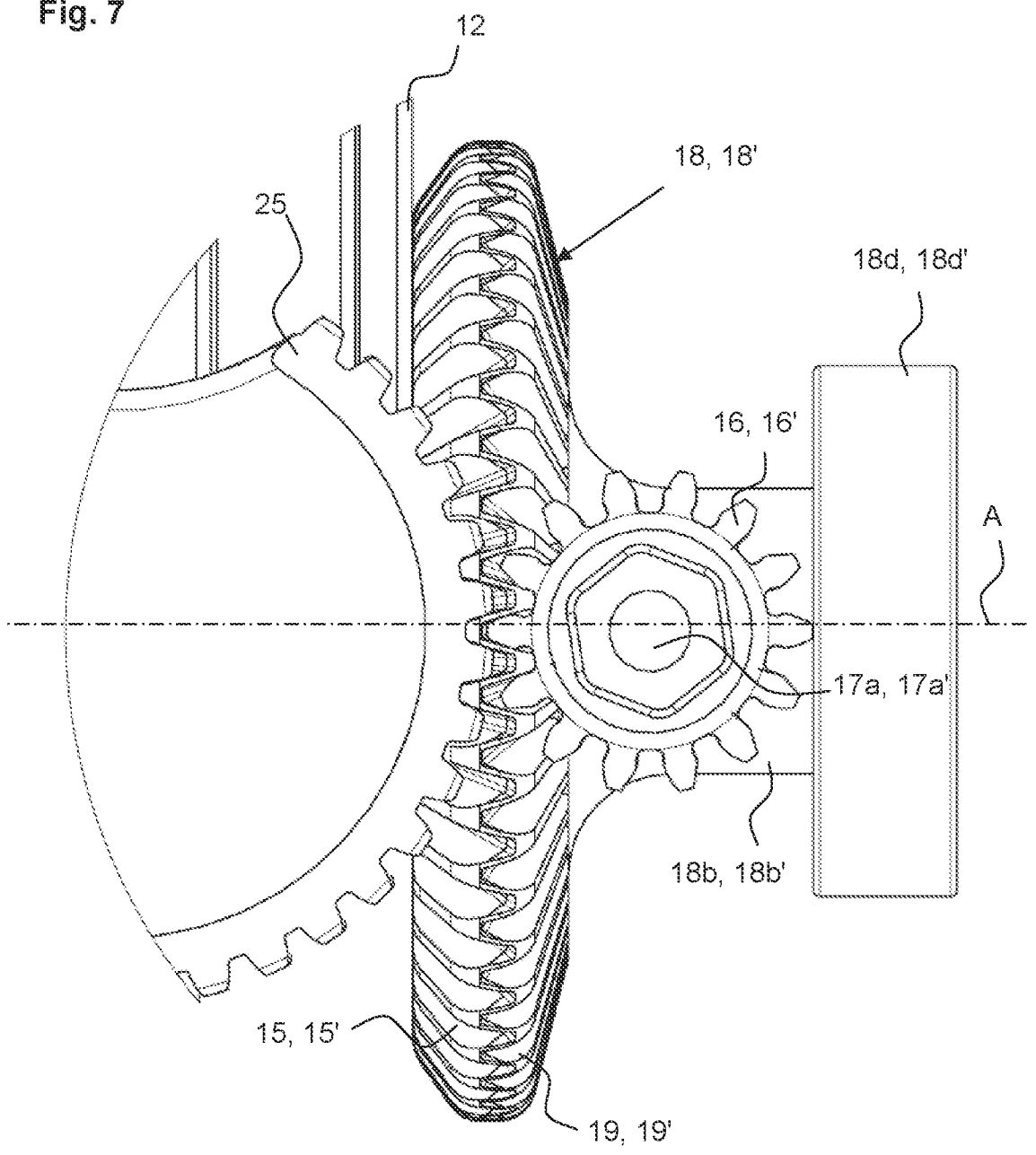

The two wheel rims 15, 15', 19, 19' of the double wheels 18, 18' have the same number of teeth, the teeth of the bevel gear rim 15, 15' and the teeth of the drive rim 19, 19' being offset from one another by half a pitch, as can be seen particularly well in FIGS. 5 and 7, so that a particularly compact double wheel is generated. The half division allows the teeth on one side to be formed from the tooth notches on the other side and the axial space requirement is extremely minimised. Since the two wheel rims 15, 15', 19, 19' are positioned back to back in this way, one-piece double wheels 18, 18' with bevel teeth on both sides are produced. This type of tooth profile also enables the components double wheel 18, 18' and drive pinion 16, 16' to be pushed together to form a particularly compact arrangement, as shown in FIGS. 2, 3 and 7.

Each double wheel 18, 18' is rotatably mounted via a corresponding mounting, as is shown in two versions in FIGS. 2 to 4. The double wheels 18, 18', which are fixedly rotatably mounted in a housing, are defined in terms of their axial location and axial position.

The double wheel 18, 18' shown in FIG. 5 shows on its side on which the drive wheel rim 19, 19' is present, a bearing axis 18b, 18b' which ends at its free end as an axis stub 18a, 18a'. The axis stub 18a, 18a' carries in FIG. 2 a bearing ring 18d, 18d', the bearing ring 18d, 18d' forming a ball bearing 18 in the example shown. This embodiment shows what is known as a double wheel-side axis stub 18a, 18a'.

The bearing ring 18d, 18d' is connected to a housing component similar to the fastening device 33 of the steering gear 13, which is shown in FIG. 4. In FIG. 4 basically another design of the bearing of the double wheels 18, 18' is shown, a so-called housing-side axis stub, wherein in FIG. 4 the visible double wheel 18 is arranged on a bearing axis 36. The bearing ring 18e of the double wheel 18 is arranged coaxially on the bearing axis 36 in a concentric bearing recess 18c of the double wheel 18, wherein the bearing ring 18e is a ball bearing 40 in the example shown. The bearing axis 36 has a thread 36a on its end facing away from the double wheel 18, 18', wherein this thread 36a is in engagement with a counter-thread 33a of a fastening device 33. The fastening device 33 is firmly connected to the housing 35 of the steering gear 13. The bearing axis 36 is formed on the housing side as a grub screw and has a notch 37 on its front face, into which a suitable tool, such as a screwdriver, can engage. With this, the bearing axis 36 can be turned in or out of the fastening device 33, as a result of which the double wheel 18 is also positioned accordingly. In this way, the distance between the double wheel 18 and the third gear wheel 25 and the fourth gear wheel 31 can be set, so that a closer or wider engagement can be set. Despite manufacturing tolerances, this adjustment option allows you to adjust the optimal gearing play for optimal performance of the gear wheel pairing: By unscrewing the bearing axis 36, the gearing becomes smoother, but with more play, and by screwing in the bearing axis 36, the gearing becomes backlash-free, but possibly a little more difficult to move. This is implemented analogously for the other double wheel 18', so that the description also applies to this. Moreover, in FIG. 4 a housing component 34*a*, which is connected to the housing 35 and surrounds the wire spreader 22, is shown with a thread that engages with a counter-thread on a cup-like housing part 34*b* that surrounds the proximal shaft end 3. The enlarged detail view shown in FIG. 4 illustrates an embodiment of the cardan coupling of the swash plate 14 to the main shaft 21, which will be described further below.

FIG. 7 shows a detailed view of the double wheel 18, 18' in the mounting arrangement in the steering gear 13 in FIG. 2, wherein the driven gear rim 15, 15' meshes with the third gear wheel 25 which is non-rotatably connected to a steering ring 30 in which the swash plate 14 is mounted. The figures do not show that the inside of the double wheel 18, 18', which is delimited by the deviation wheel rim 15, 15' and faces the steering ring 30, is concave in shape, i.e., can be arched in the direction of the bearing axis 18*b*, 18*b'*, so that the steering ring 30 has sufficient space to move for the spatial alignment of the swash plate 14 and cannot collide with the double wheel 18, 18'. The gearing of the drive pinion 16, 16', which is arranged on the drive shaft 17*a*, 17*a'*, meshes with the gearing of the drive wheel rim 19, 19'. If now the double wheel 18, 18', as FIG. 4 explained, is offset laterally along the common axis A, the engagement between the deviation wheel rim 15, 15' and gear wheel 25 can be adjusted. It is clear here that the gearing of the drive and deviation wheel rim 19, 19', 15, 15' offset by half a pitch not only achieves a more compact structure, but also prevents the teeth of the drive pinion 16, 16' from colliding with the teeth of the third gear wheel 25.

Figure 9:
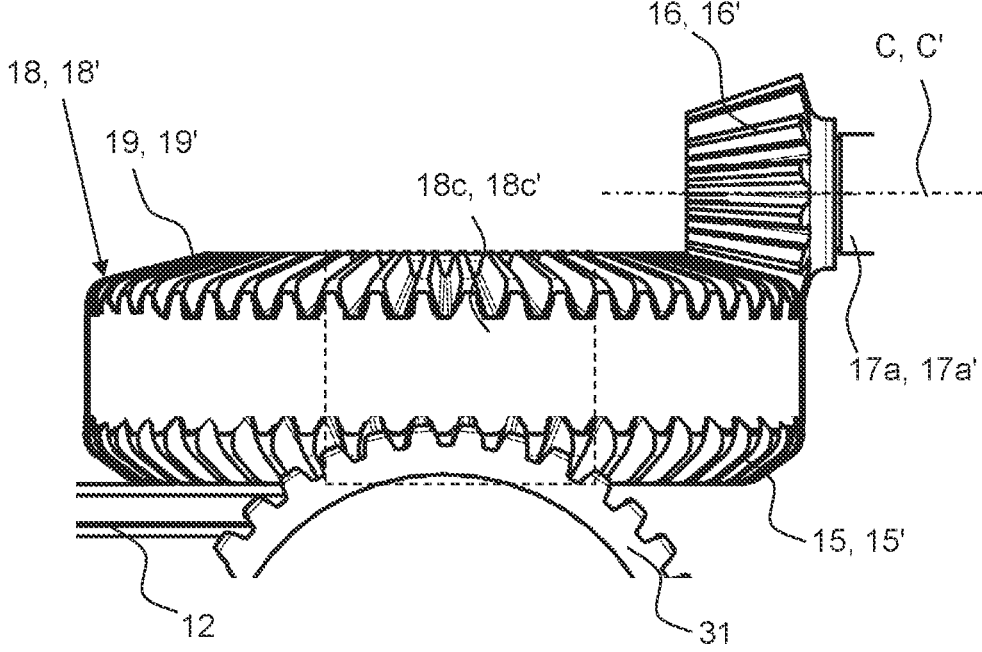
Figure 10:
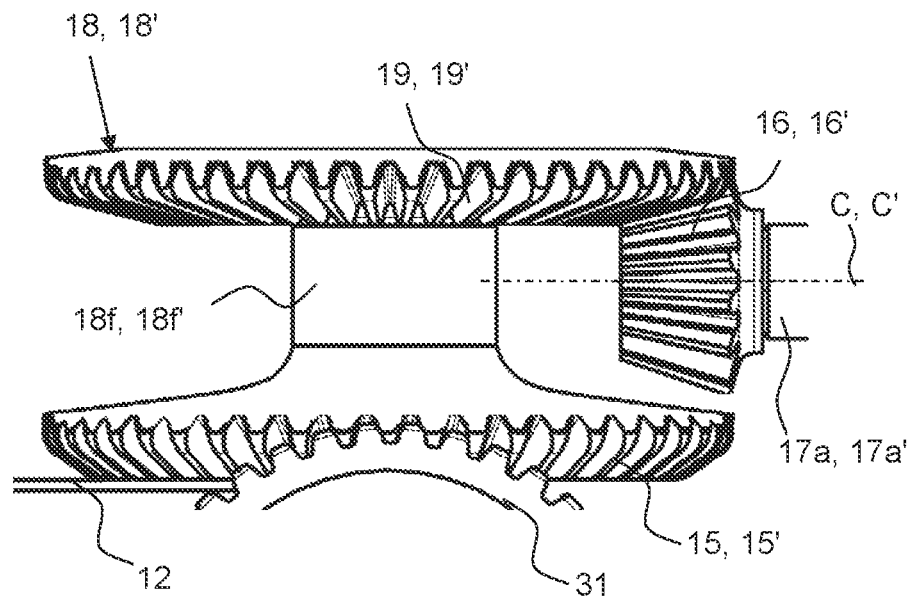

The particularly compactly constructed double wheels 18, 18' with the gearing of the drive and deviation wheel rim 19, 19', 15, 15' offset by half a pitch shown in the examples of FIGS. 2 to 7, can be used in a preferred variant of the steering gear 13, although other designs of double wheels 18, 18' are also conceivable in a steering gear 13 according to an exemplary embodiment, depending on the available installation space in the actuation unit 4, for example if a greater distance between the drive axes C, C' and the longitudinal axis B is desirable. FIGS. 9 and 10 show two examples of alternatively designed double wheels 18, 18', the double wheel 18, 18' in FIG. 9 has a greater axial distance between the drive wheel rim 19, 19' and the deviation wheel rim 15, 15', with the double wheel 18, 18' preferably having a bearing recess 18*c*, 18*c'* instead of a double-wheel bearing axis with an axis stub. In the case of the double wheel 18, 18' from FIG. 10 the axial alignment of the drive wheel rim 19, 19' is virtually reversed, so that the drive pinion 16, 16' is located between the drive wheel rim 19, 19' and the deviation wheel rim 15, 15' of the double wheel 18, 18'. For this purpose, the double wheel 18, 18' has a waist 18*f*, 18*f* in the axial direction, which spaces the deviation wheel rim 15, 15' from the drive wheel rim 19, 19', which points in the same direction as the deviation wheel rim 15, 15'. The distance provided by the waist 18*f* between the deviation wheel rim 15, 15' and the drive wheel rim 19, 19' is dimensioned such that the drive pinion 16, 16' engages in the area between the deviation wheel rim 15, 15' and the drive wheel rim 19, 19' with the drive wheel rim 19, 19'.

Depending on the design, the double wheels 18, 18' can preferably be manufactured in one piece, but multi-part double wheels 18, 18', which consist of a drive wheel with the drive sprocket and a driven wheel with the deviation sprocket, which are joined together directly or via an axle, should also be scope of protection included.

The design and operation of the steering gear 13 in relation to the activation of the swash plate 14, which can be actuated via the drive units, and their mounting are explained below with reference to FIGS. 2 to 4 and 8, where in FIG. 8 for reasons of clarity, only the deviation wheels designed as bevel gears with the bevel gear rims 15, 15' of the double wheels 18, 18' are shown.

Arranged in the shaft 2 of the instrument 1 is a hollow main shaft 21 which extends coaxially to the longitudinal axis B of the shaft 2, which can be rotated about the longitudinal axis B of the shaft 2 and extends beyond the proximal end 3 of the shaft 2 into the area of the steering gear 13. The actuation element 8 for actuating the tool 7 is mounted in an axially displaceable manner within this hollow main shaft 21.

The steering wires 12, which emerge from the shaft 2 at the proximal end 3 of the shaft 2, for which purpose a shaft end piece 3 can be provided at the proximal end of the shaft, in which passage slots 33 are provided for the steering wires 12 in the example shown, are rotationally fixed in relation to wire spreader 22 arranged on the shaft end piece 3 on the main shaft 21 and which is fanned out, as a result of which the radial distance between the steering wires 12 and the longitudinal axis B of the shaft 2 is increased. While the diameter of the bundle of steering wires 12 coaxially surrounding the longitudinal axis B of the shaft 2 within shaft 2 or at the distal end 5 in the area of the bending mechanism 9 is 4 mm, for example, the diameter of the bundle formed by the steering wires 12 behind the wire spreader 22 for example is 18 mm. The increase in the radial distance of the steering wires 12 from the longitudinal axis B of the shaft 2 achieved with the help of the wire spreader 22 not only simplifies the assembly and manufacture of the gear 13 equipped with the swash plate 14, but also the necessary adjustment angle of the swash plate 14 is reduced proportionally, in order to achieve a desired high pivoting angle of the tool tip 6. With this exemplary increase in the diameter of the steering wire bundle from 4 mm inside the shaft 2 to 18 mm behind the wire spreader 22, an adjustment angle of the swash plate 14 is correspondingly reduced by a factor of 4.5 compared to the pivoting angle of the tool tip 6 that can be achieved at the distal end. In order to bend this by 90°, it is therefore only necessary to pivot the swash plate 14 by 20°.

The steering wires 12 running parallel to the longitudinal axis B of the shaft 2 are fed to the swash plate 14 on the proximal side behind the wire spreader 22. In an alternative that is not shown, the steering wires 12 exiting at the proximal end 3 can run directly to the swash plate 14 without a wire spreader, so that the steering wires are fed to the swash plate 14 at an angle to the longitudinal axis B. To fix the steering wires 12 to the swash plate 14, through holes 23 are formed in the swash plate 14 for each steering wire 12, wherein in the example shown the steering wires 12 are positively connected and fixed within the through holes 23 via grub screws 24 with the swash plate 14. Alternative forms of fastening the steering wires to the swash plate also include, for example, welding or crimping or other clamping devices.

The double wheels 18, 18' as drive wheels are coupled to the third gear wheel 25, which is preferably designed as a bevel gear and meshes with the two bevel gear rims 15, 15' of the double wheels 18, 18', so that the axis of rotation D of the third gear wheel 25 is the common axis of rotation A of the double wheels 18 and 18' and the longitudinal axis B of the shaft 2 intersects. Due to the three gear wheels 18, 18' and 25 meshing with each other, every movement of the two double wheels 18, 18' is transmitted directly to the swash plate 14 coupled to the third gear wheel 25, which causes a direct actuation of the steering wires 12.

Figure 8:
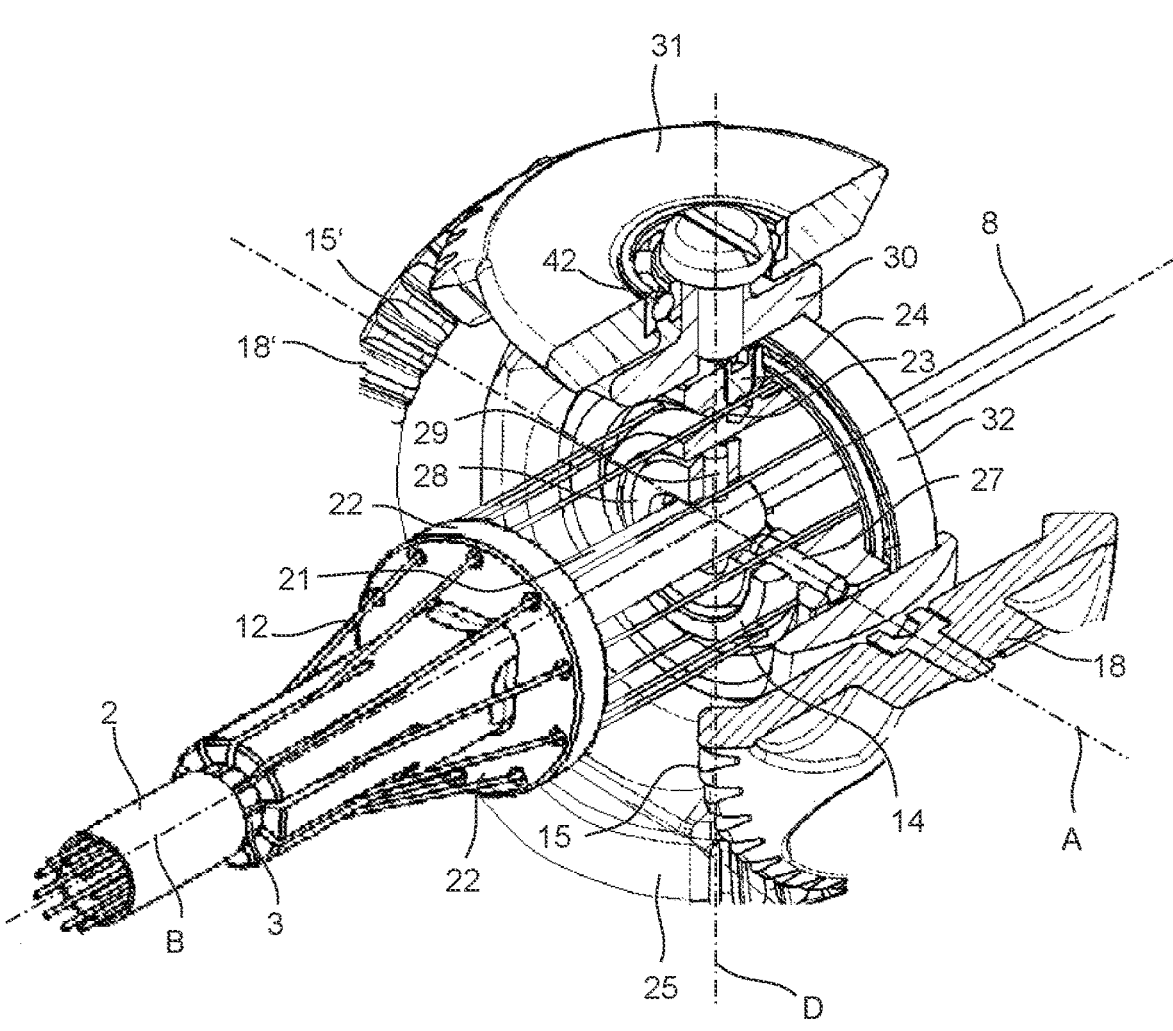

To form a cardan mounting of the swash plate 14 on the main shaft 21, the swash plate 14 in the example of FIG. 8 is pivotably mounted on a universal joint disk 28 via two bearing pins 27 offset from one another by 180°, which in turn is pivotably mounted on the main shaft 21 via two bearing pins 29 offset from one another by 180°. In FIG. 8 only one bearing pin 27 and one bearing pin 29 can be seen due to the partial sectional view.

The bearing pins 27 of the swash plate 14 and the bearing pins 29 of the universal joint disk 28 are offset by 90° to each other. This mounting makes it possible to pivot the swash plate 14 about two axes at right angles to each other relative to the longitudinal axis B of the shaft 2 and to transmit a rotation of the main shaft 21 about the longitudinal axis B to the swash plate 14, whereby by the steering wires 12 the tool tip 6 (see FIG. 1) is pivotable in all spatial directions relative to the longitudinal axis B of the shaft 2.

The steering gear 13 shown in FIGS. 2 and 4 has an alternative cardan mounting of the swash plate 14 on the main shaft 21. This bearing arrangement, which is structurally simpler, more compact and easier to assemble, also makes it possible to pivot the swash plate 14 by two degrees of freedom and to rotate it about the longitudinal axis B, whereby by the steering wires 12 the tool tip 6 can be pivoted in all spatial directions relative to the longitudinal axis B of the shaft 2. The main shaft 21 has, in the area provided for supporting the swash plate 14, two guide grooves 20a extending along the main shaft 21 and introduced on both sides or diametrically in the main shaft 21, into which two pins 29 arranged diametrically and pointing radially inwards on the swash plate 14 intervene, wherein in FIG. 2 only the guide groove 20a can be seen. This engagement allows the swash plate 14 to pivot about both the axis of rotation D and the axis of rotation A from a neutral position in which the swash plate 14 lies in a plane defined by the axis of rotation A perpendicular, i.e., at right angles to the longitudinal axis B. Superimposed movements by pivoting about both axes of rotation A, D are also possible. Further, engagement of the pins 29 with the guide grooves 20a allows a rotation angle of the main shaft 21 to be transmitted to the swash plate 14, so that the swash plate 14 can be three-dimensionally displaced relative to the longitudinal axis B of the shaft 2. The maximum tilting or torsion or the maximum tilting and rotation angles about the axis of rotation A and D are determined by the length and depth of the guide grooves 20a in conjunction with the inside diameter and strength of the swash plate 14 and the length of the pins 29. In the example of FIG. 2, the main shaft 21 has, in the region provided for supporting the swash plate 14, a spherical portion 20b on which the guide grooves 20a are provided and which fixes the swash plate 14 in the axial direction. The swash plate 14 here has a contoured receiving recess adapted to the ball section 20b.

How to continue is evident from FIGS. 2, 4 and 8, wherein the spatially adjustable swash plate 14 is mounted in a steering ring 30 coupled in a rotationally fixed manner to the third gear wheel 25. In order to close the gearing chain formed by the double wheels 18, 18' and gear wheel 25 to form a closed toothed ring, which ensures an even distribution of power, the fourth gear wheel 31 is arranged on the axis of rotation D of the third gear wheel 25, opposite the third gear wheel 25 which is also preferably engaged as a bevel gear with the bevel gear rims 15, 15' of the two double wheels 18 and 18'.

The swash plate 14 is mounted via a bearing ring 32 in the steering ring 30, which is coupled in a rotationally fixed manner to the third gear wheel 25, in order to enable the swash plate 14 to rotate about the longitudinal axis B of the shaft 2. The steering ring 30, which is coupled in a rotationally fixed manner to the third gear wheel 25, can be rotated freely in relation to the fourth gear wheel 31 by means of a bearing ring 42, so that a rotation of the fourth gear wheel 31 about its axis of rotation D does not cause any rotation of the steering ring 30 and the swash plate 14.

The described cardan mounting of the swash plate 14 on the main shaft 21 makes it possible to displace the swash plate 14 in three dimensions relative to the longitudinal axis B of the shaft 2. If, starting from the neutral initial position shown in FIGS. 2, 4 and 8, in which the swash plate 14 is aligned perpendicular to the longitudinal axis B of the shaft 2, the double wheels 18, 18' are driven via the motors 17, 17' (see FIGS. 2, 3) in such a way that the double wheels 18, 18' rotate in the same direction, this rotation of the double wheels 18, 18', due to the meshing engagement with the third gear wheel 25 and the fourth gear wheel 31, causes the structural unit, which is formed by the third gear wheel 25, the swash plate 14 coupled to the third gear wheel 25 via the steering ring 30 and the fourth gear wheel 31, to tilt about the common axis of rotation A of the double wheels 18, 18'. To simplify the functional description, the orientation of the bearing pins 27, 29 of the cardan bearing in relation to the axes of rotation A and D is referred to below. In fact, when the main shaft 21 and thus the swash plate 14 rotates, the bearing pins 27, 29 are no longer aligned with the axes A and D as shown, so that the pivot axes of the swash plate 14 provided by the bearing pins 27, 29 are different from the rotational axes A, D of the steering gear 13.

In the example of FIG. 8, the bearing pins 27, which are aligned with the axis of rotation A of the double wheels 18, 18' and via which the swash plate 14 is pivotably mounted on the universal joint disk 28, enable this tilting of the swash plate 14 relative to the main shaft 21. This tilting of the swash plate 14 about the axis of rotation A relative to the longitudinal axis B of the shaft 2 causes, via the steering wires 12, that the tool tip 6 is pivoted on the distal side relative to the longitudinal axis B of the shaft 2 in a corresponding manner. In the example of FIGS. 2 and 4 the tilting of the swash plate 14 about the axis of rotation A is made possible by the movement of the guide pins 29 in the guide grooves 20a of the main shaft 21.

If, starting from the neutral initial position shown in FIGS. 2, 4 and 8, in which the swash plate 14 is aligned perpendicular to the longitudinal axis B of the shaft 2, the double wheels 18, 18' are driven via the motors 17, 17' in such a way that the double wheels 18, 18' rotate in opposite directions, this torsion of both double gears 18, 18' due to the meshing engagement with the third gear wheel 25, causes a rotation of the structural unit, which is formed from the third gear wheel 25 and the swash plate 14 coupled to the third gear wheel 25 via the steering ring 30, about the axis of rotation D of the third gear wheel 25.

In the example of FIG. 8 the bearing pins 29 aligned with the axis of rotation D of the third gear wheel 25 allow for, via which the universal joint disk 28 is pivotably mounted on the main shaft 21, together with the free rotatability of the swash plate 14 relative to the fourth gear wheel 31 due to the steering ring 32, this relative rotation of the universal joint disk 28 to the main shaft 21. This rotation of the swash plate 14 about the axis of rotation D relative to the longitudinal axis B of the shaft 2 causes, via the steering wires 12, that the tool tip 6 is pivoted on the distal side relative to the longitudinal axis B of the shaft 2 in a corresponding manner. Analogously, in the example of FIGS. 2 and 4 the rotation of the swash plate 14 about the axis of rotation D is brought about by the pins 29 engaging in the guide grooves 20*a* and aligned with the axis of rotation D of the third gear wheel 25.

It is of course possible to superimpose the movements described so that, for example, the swash plate 14 is tilted about the common axis of rotation A of the double wheels 18, 18' and at the same time is rotated about the axis of rotation D of the third gear wheel 25. The combination of the two movement sequences due to the individually controllable motors 17, 17' of the gear 13 and the coupling with the main shaft 21 allows the swash plate 14 to be three-dimensionally adjusted relative to the longitudinal axis B of the shaft 2, resulting in a corresponding spatial displacement of the tool tip 6 due to the coupling via the steering wires 12.

A surgical instrument 1 designed as described above is characterised in that many thin guide wires 12 can be used to control the pivotable tool tip 6, and this control due to the motorised drive 13 for the swash plate 14, on which the guide wires 12 are mounted, sensitive, exact and reproducible.

LIST OF REFERENCE NUMBERS

1 Surgical instrument
2 Shaft
3 Proximal end (shaft)/shaft end piece
4 Actuation unit
5 Distal end (shaft)
6 Tool tip
7 Instrument tool
8 Actuation element
9 Bending mechanism
10 Drive unit (swash plate)
11 Pivoting member
12 Guide wire
13 Steering gear
14 Swash plate
15, 15' Deviation wheel rim Double wheels 18,18'
16, 16' Drive pinion
17, 17' Motor
17*a*, 17*a*' Drive shaft Motors
18, 18' Double wheel
18*a* Axis stub
18*b* Bearing axle
18*c* Bearing recess
18*d* Bearing ring
18*e* Bearing ring
18*f* Waist
19,19' Drive wheel rim Double wheels 18,18'
20*a*, 20*b* Guide groove, ball section
21 Main shaft
22 Wire Spreader
23 Through holes

24 Grub screws
25 Third gear wheel
27 Bearing pins
28 Universal joint disk
29 Bearing pins
30 Steering ring
31 Fourth gear wheel
32 Bearing ring
33 Fastening device
33*a* Counter-thread
34*a*,*b* Housing component
35 Housing component
36 Housing-side bearing axis
36*a* Thread
37 Notch
40 Bearing
42 Bearing ring
A Common axis of rotation of the driven double gear wheels 18,18
B Longitudinal axis of the instrument or the shaft
C Drive axis of the first drive 17
C' Drive axis of the second drive 17'
D Axis of rotation of the third and fourth gear wheel

The invention claimed is:

1. A steering gear configured for use with a surgical instrument, the steering gear configured to be arranged at the proximal end of a shaft that defines a longitudinal axis with a bending joint at the distal end of the shaft, the steering gear comprising:

two motorized drives configured to spatially align a swash plate via adjustment angles of the two drives, the steering gear configured to control a distal bending joint of the surgical instrument, wherein:

a first drive of the two motorized drives has a first drive pinion configured to be driven by a first motor via a first drive shaft which defines a first drive axis and which is connected to a first drive wheel rim of a first drive wheel in operative connection, a second drive of the two motorized drives has a second drive pinion configured to be driven by a second motor via a second drive shaft which defines a second drive axis and is connected to a second drive wheel rim of a second drive wheel in operative connection, the first and the second drive wheels are double wheels with two, parallel bevel gear rims, the first drive wheel having the first drive wheel rim on a first side, and a first deviation wheel rim on a second, opposite side, the second drive wheel having the second drive wheel rim on a first side, and a second deviation wheel rim on a second, opposite side, and between the two drive wheels, which have a common axis of rotation, the swash plate is arranged, and the deviation wheel rims are arranged with the second opposite sides facing each other on the axis of rotation, and the swash plate is coupled to a third gear wheel, which meshes with the two deviation wheel rims of the first and second drive wheels, and whose axis of rotation is at right angles to the common axis of the double wheels.

2. The steering gear according to claim 1, wherein at least one of first and second drive pinions is a bevel pinion, and at least one of the first and second drive wheel rims and the deviation wheel rims are the two, parallel bevel gear rims, and the deviation wheel rims and the drive wheel rims are on opposite sides of the respective double wheels, and teeth of each of the deviation wheel rims and teeth of the drive wheel rims are offset from one another by half a pitch.

3. The steering gear according to claim 1, wherein: the drive pinion is a bevel pinion, and the double wheels each have a waist in the axial direction, which respectively spaces the deviation wheel rim from the drive wheel rim, which points in the direction of the deviation wheel rim, wherein the distance provided by the respective waists between the deviation wheel rim and the drive wheel rim are dimensioned such that the drive pinion is arranged in the area of the waist between the respective deviation wheel rim and the drive wheel rim.

4. The steering gear according to claim 1, wherein each double wheel is arranged on a bearing axis, which is an axis stub at a free end pointing away from the double wheel, which carries a bearing ring, wherein the bearing ring is a ball bearing or a roller bearing.

5. The steering gear according to claim 1, wherein each double wheel is arranged on a bearing axis, wherein a bearing ring is arranged coaxially on the bearing axis in a concentric bearing recess of the double wheel, and wherein the bearing ring is a ball bearing or a roller bearing.

6. The steering gear according to claim 5, wherein the bearing axis has a thread at a free end pointing away from the double wheel, which thread engages with a counter-thread of a fastening device, the fastening device being connected to a housing component of the steering gear.

7. The steering gear according to claim 1, wherein the swash plate is coupled to a fourth gear wheel which is coupled to the two deviation wheel rims of the two double wheels and arranged on the side facing away from the third gear wheel.

8. The steering gear according to claim 1, wherein the drive pinion and the drive wheel rim form a bevel helical gear or hypoid gear.

9. The steering gear according to claim 1, wherein each of the motors are arranged via their respective drive pinion in any position pointing radially away from the respective drive wheel rim, with the two drive axes running parallel to each other.

10. A surgical instrument having a shaft and a tool arranged at the distal end of the shaft with a tool tip that is configured to be bent and is configured to be controlled by the swash plate that is spatially aligned by the two drives, wherein
the surgical instrument has a steering gear according to claim 1, which has the two drives and is configured to transfer the adjustment angles of the two drives to the spatial alignment of the swash plate.

11. The surgical instrument according to claim 10, wherein
the swash plate is coupled to the third gear wheel which meshes with the two deviation wheel rims of the two double wheels about the longitudinal axis of the shaft is rotatably mounted in a steering ring via a bearing ring, which is coupled in a torque-proof manner to the third gear wheel, wherein the swash plate is cardan coupled with a main shaft coaxially extending to a longitudinal axis of the shaft.

12. The surgical instrument according to claim 10, wherein
the swash plate is pivotably mounted on a universal joint disk via two bearing pins arranged offset from one another by 180°, wherein the universal joint disk is pivotably mounted on the main shaft via two bearing pins arranged offset from one another by 180°, and wherein the bearing pins of the swash plate and of the universal joint disk are arranged offset from one another by 90°,
or a cardan bearing is provided by two longitudinally extending guide grooves diametrically present in the main shaft and two pins arranged diametrically and pointing radially inwards on the swash plate, each pin engages in one of the guide grooves, so that an angle of rotation of the main shaft is transferred to the swash plate.

13. The surgical instrument according to claim 10, wherein
in the longitudinal direction of the shaft, steering wires run which are connected to the swash plate of the steering gear.

14. The surgical instrument according to claim 11, wherein
a fourth gear is coupled to the swash plate via another bearing ring, wherein the fourth gear is freely rotatable with respect to the third gear wheel.

15. The surgical instrument according to claim 13, wherein
an actuation element is mounted in the shaft in an axially displaceable manner and is operatively connected to the actuation unit on a proximal side, and the distal bending joint of the bendable tool tip extends from the distal end of the shaft.

16. The surgical instrument according to claim 13, wherein
a radial distance of the steering wires from the longitudinal axis of the shaft on the swash plate is greater than at the proximal end of the shaft from which the steering wires emerge, wherein
the steering wires extend from the proximal end of the shaft directly to the swash plate, the steering wires running at an angle deviating from 90° to the swash plate, or
a wire spreader is arranged on the main shaft on the distal side in front of the swash plate, which increases the radial distance of the steering wires from the longitudinal axis of the shaft, so that the steering wires run parallel to one another between the wire spreader and the swash plate and form an angle of 90° with respect to a disk surface of the swash plate.

17. A steering gear configured for use with a surgical instrument comprising:
two parallel motorized drives configured to spatially align a swash plate via adjustment angles of the two drives, the steering gear configured to control a distal bending joint of the surgical instrument, wherein:
a first drive of the two motorized drives has a first drive pinion gear configured to be driven by a first motor via a first drive shaft which defines a first drive axis and which is connected by gearing to a first drive wheel rim of a first drive wheel,
a second drive of the two motorized drives has a second drive pinion gear configured to be driven by a second motor via a second drive shaft which defines a second drive axis and is connected by gearing to a second drive wheel rim of a second drive wheel,
the first and the second drive wheels are double wheels with two, parallel bevel gear rims, the first drive wheel having the first drive wheel rim on a first side that engages with the first drive pinion gear, and a first deviation wheel rim on a second, opposite side, the second drive wheel having the second drive wheel rim on a first side that engages with the second drive pinion gear, and a second deviation wheel rim on a second, opposite side, and between the two drive wheels, which have a common axis of rotation, the swash plate is arranged, and the deviation wheel rims are arranged with the second opposite sides facing each other on the axis of rotation, and the swash plate is coupled to a third gear wheel, which meshes with the two deviation wheel rims of the first and second drive wheels, and whose axis of rotation is at right angles to the common axis of the double wheels.

\* \* \* \* \*